(12) United States Patent
Cole et al.

(10) Patent No.: US 9,907,553 B2
(45) Date of Patent: Mar. 6, 2018

(54) STAPLER FOR FORMING MULTIPLE TISSUE PLICATIONS

(71) Applicant: Boston Scientific Scimed, Inc., Maple Grove, MN (US)

(72) Inventors: David Cole, San Mateo, CA (US); Jesica Ferro, Redwood City, CA (US); Bretton Swope, Gaithersburg, MD (US); Tyler Grubb, Denver, CO (US); Daniel Balbierz, Redwood City, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 675 days.

(21) Appl. No.: 14/479,542

(22) Filed: Sep. 8, 2014

(65) Prior Publication Data
US 2014/0374465 A1    Dec. 25, 2014

Related U.S. Application Data

(63) Continuation of application No. PCT/US2013/049125, filed on Jul. 2, 2013.
(Continued)

(51) Int. Cl.
*A61B 17/068* (2006.01)
*A61B 17/072* (2006.01)
(Continued)

(52) U.S. Cl.
CPC ...... *A61B 17/068* (2013.01); *A61B 17/07292* (2013.01); *A61B 17/1155* (2013.01);
(Continued)

(58) Field of Classification Search
CPC .................. A61B 17/1155; A61B 2017/07271
See application file for complete search history.

(56) References Cited

U.S. PATENT DOCUMENTS

| 5,937,951 A | 8/1999 | Izuchukwu et al. |
| 7,708,181 B2 * | 5/2010 | Cole ................ A61B 17/115 227/175.2 |

(Continued)

FOREIGN PATENT DOCUMENTS

| CN | 101224125 A | 7/2008 |
| EP | 0156774 A2 | 10/1985 |

(Continued)

*Primary Examiner* — Andrew M Tecco
(74) *Attorney, Agent, or Firm* — Bookoff McAndrews, PLLC

(57) ABSTRACT

A stapling device for forming multiple tissue plications without needing to reload the device between plications is described. The device includes staple and anvil housings that move toward and away from a tissue-capture position. A cartridge holder in the staple housing supports a cartridge with multiple groups of offset staple slots, where the slots in each group are circularly arrayed about a cartridge center axis. A staple driver in the staple housing carries a plurality of arms for engaging and ejecting the staples in a first group of staples in the cartridge, when a tissue fold is captured between the cartridge assembly and anvil in the anvil housing. When the staple driver is retracted, after a tissue plication is formed, the cartridge assembly and tissue drive are indexed to eject the next-up group of staples.

20 Claims, 13 Drawing Sheets

Related U.S. Application Data

(60) Provisional application No. 61/667,376, filed on Jul. 2, 2012.

(51) Int. Cl.
*A61B 17/115* (2006.01)
*A61B 17/00* (2006.01)
*A61B 17/30* (2006.01)

(52) U.S. Cl.
CPC ............ *A61B 2017/00539* (2013.01); *A61B 2017/00876* (2013.01); *A61B 2017/07271* (2013.01); *A61B 2017/306* (2013.01)

(56) References Cited

U.S. PATENT DOCUMENTS

| | | | | |
|---|---|---|---|---|
| 7,934,631 | B2* | 5/2011 | Balbierz | A61B 17/068 227/176.1 |
| 8,469,977 | B2* | 6/2013 | Balbierz | A61B 17/068 227/176.1 |
| 2007/0219571 | A1* | 9/2007 | Balbierz | A61F 5/0036 606/153 |
| 2008/0169329 | A1 | 7/2008 | Shelton et al. | |
| 2009/0236401 | A1* | 9/2009 | Cole | A61B 17/115 227/180.1 |
| 2010/0116867 | A1* | 5/2010 | Balbierz | A61B 17/068 227/175.1 |
| 2010/0191282 | A1 | 7/2010 | Harris et al. | |
| 2011/0192881 | A1* | 8/2011 | Balbierz | A61B 17/068 227/176.1 |

FOREIGN PATENT DOCUMENTS

| | | |
|---|---|---|
| JP | 2-58936 | 12/1990 |
| JP | 2010-504811 | 2/2010 |
| JP | 2011-515158 | 5/2011 |
| JP | 2012-508078 | 4/2012 |
| WO | WO 83/00614 | 3/1983 |
| WO | WO 2008/042022 A1 | 4/2008 |
| WO | WO 2008/141288 A1 | 11/2008 |
| WO | WO 2009/117533 A2 | 9/2009 |
| WO | WO 2010/054404 A1 | 5/2010 |

* cited by examiner

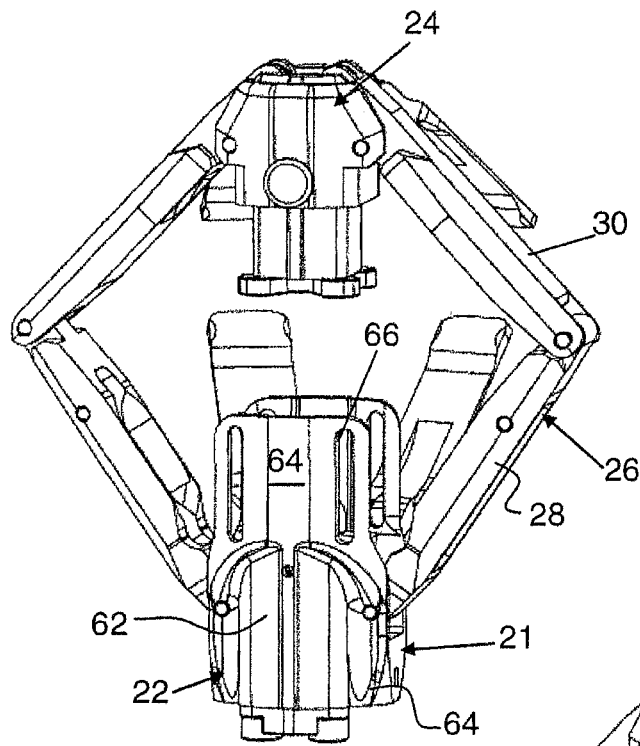
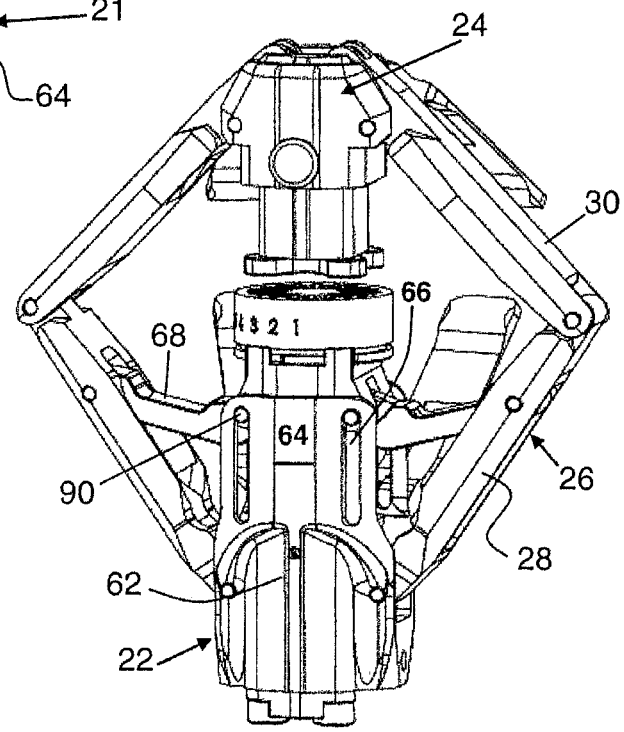
Fig. 4A
Fig. 4B

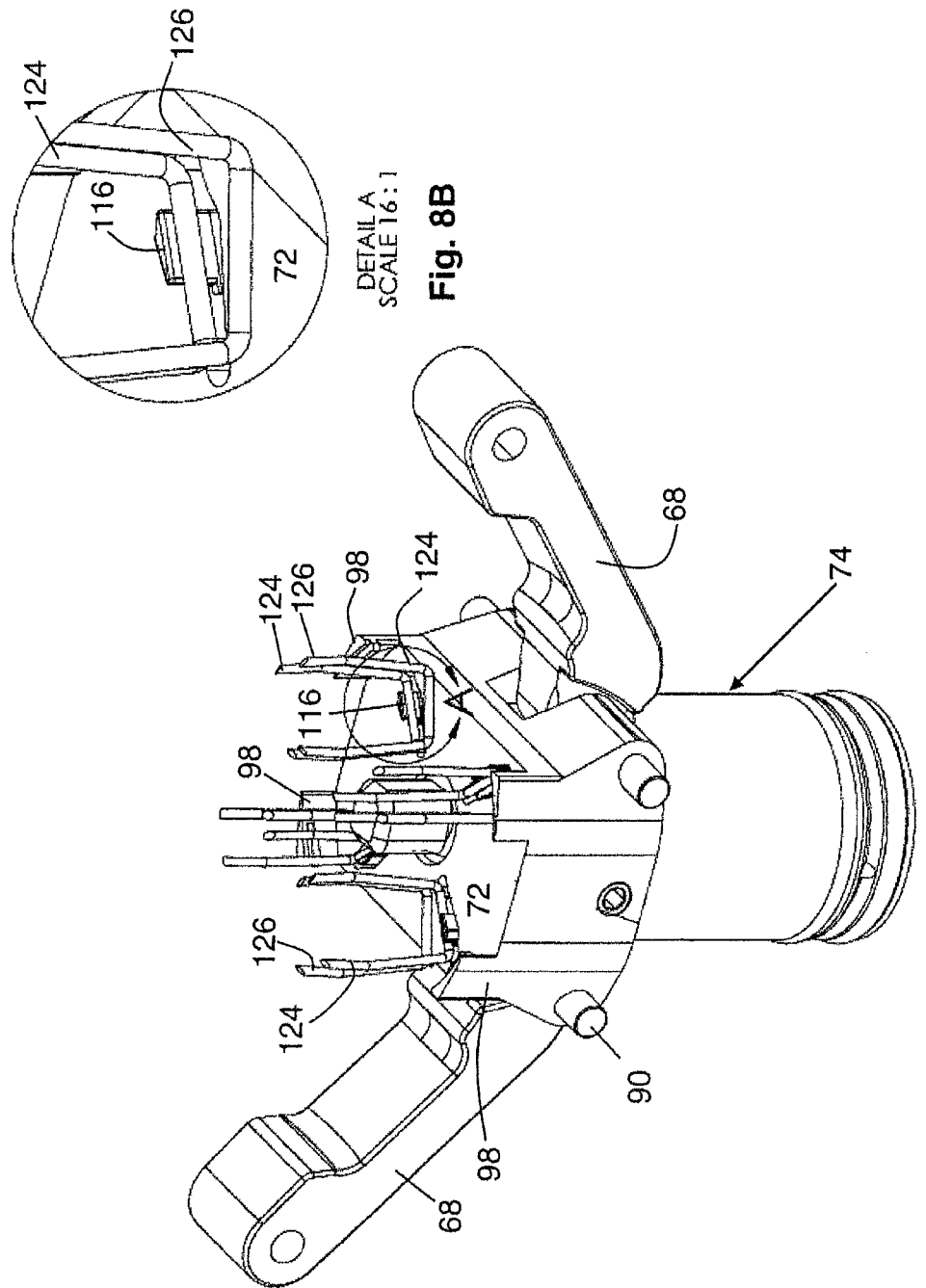

STAPLER FOR FORMING MULTIPLE TISSUE PLICATIONS

This application is a continuation of pending International Application No. PCT Application No. PCT/US2013/049125, filed Jul. 2, 2013, which claims benefit of priority from U.S. Provisional Application No. 61/667,376, filed Jul. 2, 2012, all of the aforementioned applications are hereby incorporated by reference.

FIELD OF THE INVENTION

The present invention relates generally to the field of stapling devices, and in particular, devices that can be used for endoscopic stapling of tissue within body cavities.

BACKGROUND OF THE INVENTION

A standard procedure for the treatment of obesity and obesity-related diabetes to reduce stomach volume, either surgically or by forming stapled folds or tissue plications within the stomach. Co-owned U.S. Pat. Nos. 8,020,741, 7,922,062, 7,913,892, 7,909,223, 7,909,222, 7,909,219, and 7,708,821, for example, disclose an endoscopic stapling device that can be inserted into a patient's stomach intraorally, and operated to draw a section of stomach into a fold and staple the fold with a circular array of staples to form a tissue plication within the stomach. Ideally, in order to reduce total stomach volume sufficiently, e.g., to less than half of the original volume, it is necessary to create a number of such plications, typically between about 8 and 15. This requires that the stapling device be removed from the stomach after each plication is formed, reloaded with a fresh array of staples, introduced into the patient's stomach again, and then operated to form a new plication. A stomach-reduction procedure that requires 10 such plications would thus require the physician to insert and remove the stapling device a total of ten times during the entire procedure. This is both time-consuming, and uncomfortable to the patient, and adds to the risk of injuring the patient's stomach as the device is being inserted into the stomach.

It would therefore be desirable to provide a stapler device that can be used by a physician to produce multiple stapled tissue plications without needing to reload the device between successive plications.

SUMMARY OF THE INVENTION

The invention includes in one aspect, a stapling device for use in producing multiple stapled tissue plications without needing to reload. The device includes, in operative condition, a stapler head composed of a staple housing having a cartridge assembly support mounted therein for holding a staple cartridge assembly, a cartridge assembly held on said support and comprising a cartridge having multiple groups of offset staple slots, where the slots in each group are circularly arrayed about a cartridge assembly center axis and are oriented outwardly with respect to said axis, and staples held in the slots, and a staple driver mounted in the housing for movement between retracted and extended positions. The driver includes a pusher having a plurality of pusher arms for engaging the staples in a first group of staples in the cartridge, and ejecting such staples from the cartridge, when the pusher driver is moved from a retracted toward an extended position. An indexing mechanism in the staple housing advances the staple cartridge relative to the staple pusher, to position a next-up group of staples in the cartridge for engagement with associated arms in the pusher, after the staples in the previous group have been ejected from the cartridge. The staple housing and an anvil housing in the device are mounted for relative movement with respect to one another, under the control of a housing driver in one in one of the housings, toward and away from a stapling position at which a tissue fold disposed between the two housings is captured for stapling between the cartridge assembly and an anvil in the anvil housing. Successive stapled tissue folds can be formed without reloading the device by successively stapling tissue folds captured between the cartridge assembly and anvil with staples from successive offset groups of staples in the cartridge assembly. The staple cartridge may be releasably attached to the support.

In one embodiment, the cartridge in the assembly has an outer surface, the staples in the cartridge each have a pair of free ends projecting from the cartridge's outer side, and the cartridge assembly includes multiple reinforcing rings stacked against the cartridge's outer side, where each ring has a plurality of circularly arrayed eyelets for receiving therein, one or both of the free ends of the staples in a given staple group, such that one ring is stacked against the cartridge assembly for each group of staples, and the groups of staples are ejected in the order of the stacked rings, in an outer to inner direction.

The cartridge may include N groups of M slots each, where N and M are each at least 3, and N×M is at least twelve.

The pusher arms may provide troughs into which the staples are received during a staple ejection operation, and the troughs may have rounded sides for guiding the staples into the centers of the troughs.

In one embodiment, the cartridge is mounted on the cartridge assembly support for angular movement with respect to the support, and the indexing mechanism includes a torsion spring operatively interposed between the support and the cartridge, for advancing the cartridge to a next-up indexing position when the staples in a previous group of staples have been ejected and as the pusher is moved toward its retracted position. The indexing mechanism may further include a tab on at least one of the pusher arms that engages at least one of the staples the in next-up group of stapler in the cartridge as the pusher is moved toward its retracted position.

In another embodiment, the cartridge assembly is mounted on the cartridge holder at a fixed position, and the indexing mechanism includes a torsion spring operatively interposed between the cartridge and staple driver, for advancing the pusher arms to a next-up indexing position in the cartridge when the staples in a previous group of staples have been ejected and as the pusher is moved toward its retracted position. The indexing mechanism may further include a tab at least one of the pusher arms that engages the next-up slot on the cartridge assembly as the pusher is moved toward its retracted position.

The staple cartridge may be a cylindrical magazine whose multiple groups of offset staple slots extend through the cartridge assembly and are tapered at the bottom of the slots to retain the staples therein. The slots formed in the cartridge may extend along radii projecting from the central axis of the cartridge. Alternatively, the slots formed in the cartridge may be radially offset from one another, such that a radial line that intersects the inner end of a slot intersects a second slot between its inner and outer ends.

The staples carried in the cartridge may be U-shaped, where the staple legs are bowed outwardly, such that the legs taper inwardly on progressing toward the base of the staple, and taper inwardly on progressing toward the free ends of the staples.

The anvil may include a plurality of anvil surfaces, one for each staple in a group, and each surface may include a pair of side-by-side grooves for bending a staple being ejected against the anvil so that the ends of the staples are bent into a side-by-side overlapping configuration.

The staple and anvil housings may be mounted by an arm assembly in the device, for movement toward and away from one another, where said housing driver operatively couples the staple housing to the arm assembly, such that movement of the housing drive from a retracted toward an extended position causes the arm assembly to spread outwardly and move the anvil housing relatively toward the staple housing. The arm assembly may include at least a pair of arms, each of which pivots outwardly as the anvil housing is drawn relatively toward the staple housing, where arms form, along with confronting surfaces of the staple cartridge assembly and anvil, a tissue chamber that expands outwardly as the two housing are drawn toward one another. The device may further include a membrane covering said chamber, allowing tissue to be drawn into the chamber, with application of a vacuum to the membrane. The device may further includes at least one arm spreader pivotally connecting said staple holder to the arm assembly, for spreading the arm assembly outwardly as the staple housing is moved relatively toward the anvil housing. The anvil housing may further includes drive links operatively connecting the arm assembly to the anvil, for advancing the anvil within the anvil housing toward the staple housing as the staple housing is moved relatively toward the anvil housing.

For use in forming multiple stapled tissue plication in a patient's stomach, the device may further include a elongate flexible shaft having a distal end operatively connected to the staple housing, a proximal end having user controls, and torque-transmission cables carried within the shaft for transmitting torque from a selected user control to a selected drive screw of the drive assembly, where the shaft is being dimensioned for intraoral access to selected patient stomach regions.

In another aspect, the invention includes a staple cartridge assembly for use with a stapling device for producing multiple stapled tissue plications without needing to reload the device between successive plications. The assembly includes (a) a staple cartridge having multiple groups of offset staple slots, where the slots in each group are circularly arrayed about a cartridge center axis and are oriented outwardly with respect to said axis, (b) staples held in the slots, and having a pair of free ends that extend from an outer surface of the cartridge, and (c) multiple reinforcing rings stacked against the cartridge's outer surface, each ring having a plurality of circularly arrayed eyelets for receiving therein, the free ends of the staples in a given staple group, such that one ring is stacked against the cartridge assembly for each group of staples, and the groups of staples are ejected in the order of the stacked rings, in an outer to inner direction.

The staple cartridge may be a cylindrical magazine whose multiple groups of offset staple slots extend through the cartridge assembly and are tapered at the bottom of the slots to retain the staples therein, where the slots may be radially projecting or radially offset, as above.

In another aspect, the invention includes a stapling device for use in producing multiple stapled tissue plications without needing to reload. The device has the elements and operations described above except that (a) the cartridge has multiple angularly offset staple slots, and (b) the staple driver has a pusher having a single pusher arm for engaging a single in the cartridge, thus to form multiple tissues plications, each fastened with a single staple.

These and other objects and features of the invention will become more fully apparent when the following detailed description of the invention is read in conjunction with the accompanying drawings.

BRIEF DESCRIPTION OF THE DRAWINGS

FIGS. 4A and 4B are side views of a stapler device with the piston subassembly hidden (4A) and shown (4B);

FIGS. 8A and 8B show detail of a staple pusher in the device catching on a staple back in order to stop cartridge rotation and align the staples for firing (8A) and detail of the region A in the FIG. 8B);

DETAILED DESCRIPTION OF THE INVENTION

I. Overview of the Staple Device and its Operation

This section gives an overview of the components and operation of an embodiment of a staple device intended for forming multiple tissue plications in a patient's stomach, for example, in treating obesity or obesity-related diabetes, or in repairing an earlier stomach-reduction surgery. Details of the construction and operation of the device, and the construction of alternative embodiments, are given in the sections below.

Figure 1:
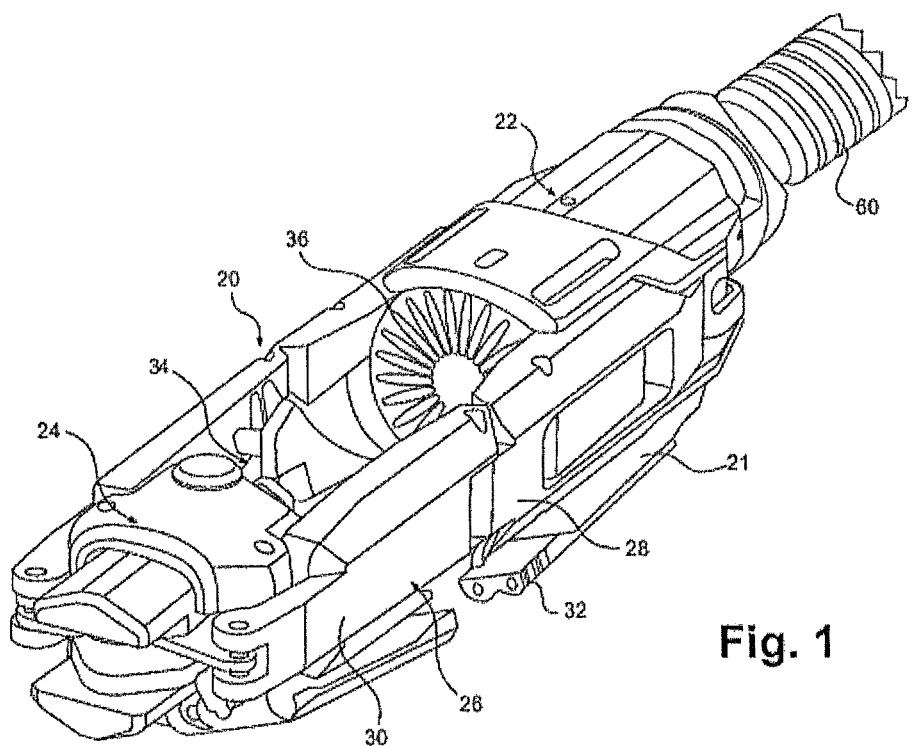
FIG. 1 is a perspective view of a multi-fire stapling device constructed in accordance with an embodiment of the invention.

The stapler device is indicated at 20 in FIG. 1, and includes a staple head 21 composed of a staple housing 22 and an anvil housing 24. The two housings are joined, on their opposite sides, for relative movement toward and away from one another other, by a pair of arm assemblies 26. Each arm assembly includes a pair of arms 28, 30 pivotally attached at exterior ends to the staple housing and anvil housing, respectively, and pivotally attached to each other at the interior arm ends. The two housings are also joined at their lower surfaces in the figure by a two-section expansion bar 32. The combination of the inwardly facing ends of the two housings, the arm assemblies connecting the two housings, and the expansion bar form a tissue chamber 34 that is covered by a clear, flexible membrane (not shown). During a plication-forming operation, the two housings are moved toward one another, causing the arm assemblies to pivot outwardly and the expansion bar to bend outwardly, expanding the width and height of the tissue chamber as tissue is being drawn into the chamber, under a vacuum applied to the device, through an opening in the upper surface of the flexible membrane in the figure. The rate of movement of the two housings toward one another and the rate of vacuum applied to the chamber during a tissue-capture operation are controlled to allow the tissue fold forming in the chamber to substantially fill the height and width dimensions of the chamber.

Figure 2:
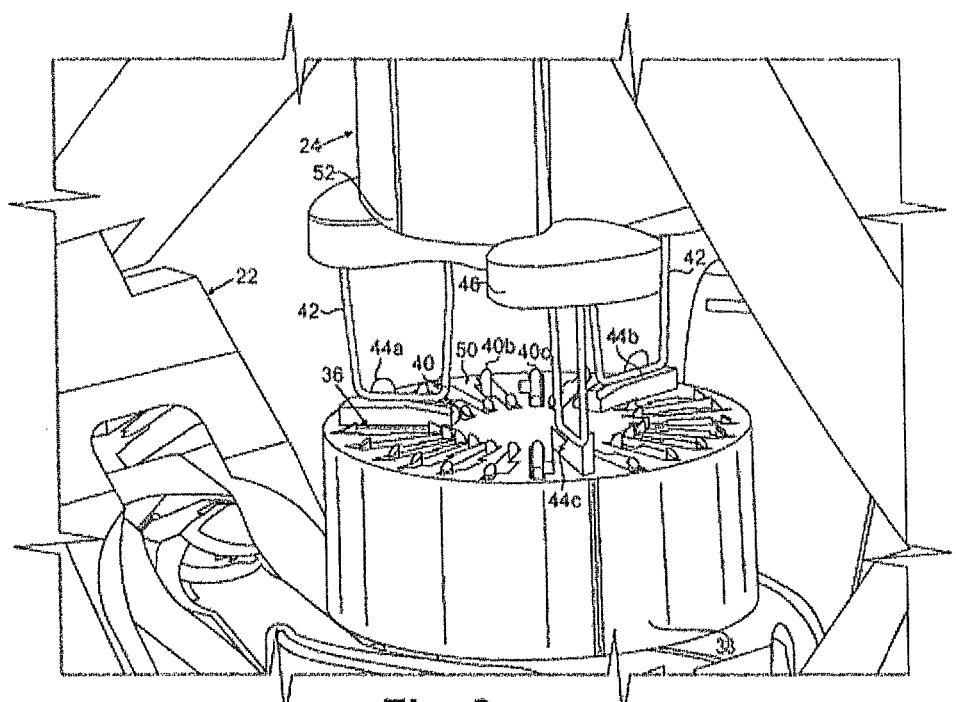
FIG. 2 is a perspective view of a staple ejection operation in the device.

With reference to FIGS. 1 and 2, a staple cartridge assembly 36 in the device is carried in the staple housing on a cartridge support, as detailed below with reference to FIGS. 5A and 5B. As seen best in FIG. 2, a cartridge 38 in assembly 36 is a cylindrical magazine having a circular array of staples slots, such as slots 40a, 40b, 40c, for receiving staples, such as staples 42, therein. The slots can be thought of as forming N groups or M slots each, where the slots in any one group are circularly arrayed about the cartridge, and separated by slots in the other N−1 groups. Thus, for example, the 24 slots in cartridge 38 could form 8 groups of 3 slots each, where a group would include every third slot in the cartridge, or 6 groups of 4 slots, where a group would include every fourth slot in the cartridge, and so forth. Cartridges having different numbers of slots and slot configurations are described below with reference to FIGS. 12A-12D.

As shown in FIG. 2, a staple driver in the staple housing, described below with reference to FIGS. 5A and 5B, has a plurality of pusher arms, such as arms 44a, 44b, 44c, for ejecting the staples in a group (in this case, a group of three staples) out of the cartridge and through a tissue fold (not shown) captured between the cartridge assembly and an anvil 46 in anvil housing 24. The cartridge assembly and anvil are typically spaced from one another by a distance of about 0.06 and 0.11 inches at their tissue-capture positions, depending on staple size, and are thus spaced closer to one another than indicated in FIG. 2 at the tissue-capture position. During ejection, the staples are forced through the captured tissue fold and bent inwardly on contact with the anvil to crimp the staples. After staples have been ejected from the cartridge, an indexing mechanism operates to advance either the cartridge or the pusher arms so that the pusher arms are now aligned to engage the staples in the next-up group of slots in the cartridge, as will be described below. With vacuum released from the chamber, the stapled tissue fold is also released, and the device is set to capture and staple a new tissue fold.

Figure 3A:
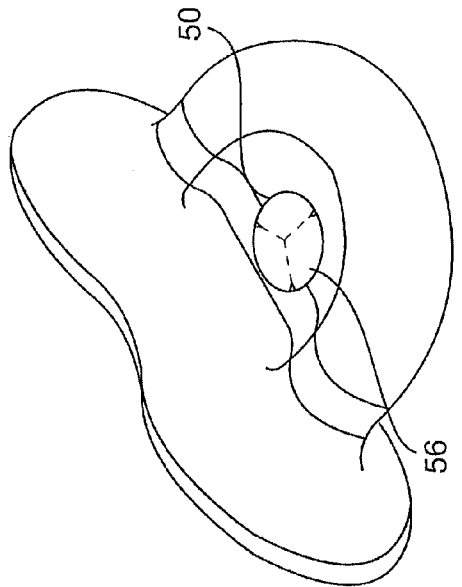
FIGS. 3A-3C show exemplary tissue-fold plications formed with eight staples (1A), three staples (1B) and 4 staples (1C).
Figure 3B:
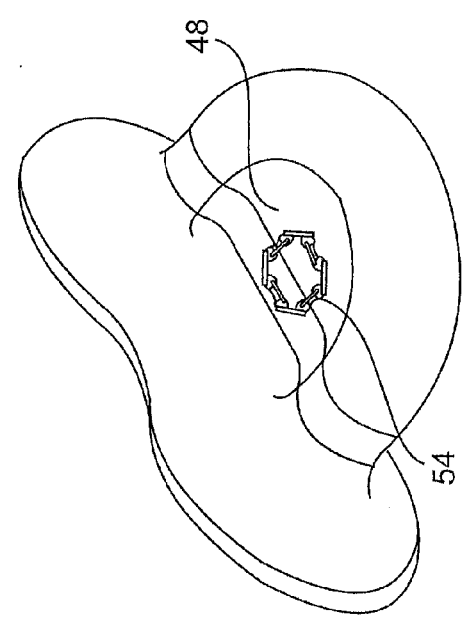
Figure 3C:
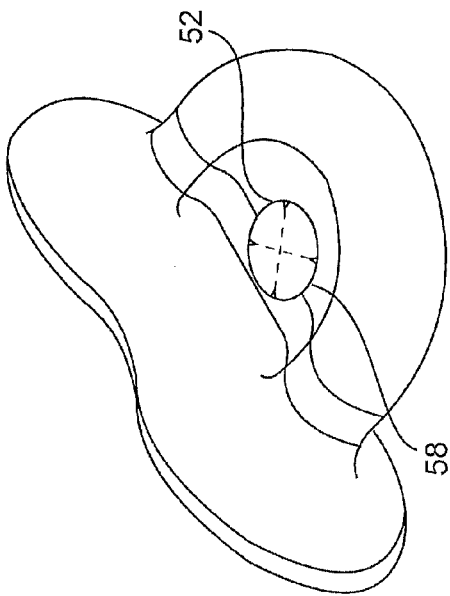

As can be appreciated from FIG. 2, the embodiment illustrated is designed to staple a tissue fold with three circularly arrayed staples, allowing up to 8 plications to be produced without reloading. Simply by varying the number of pusher arms in the pusher driver, the same device can be adapted for making 6 folds with 4 staples each, 4 folds with 6 staples each or 3 folds with 8 staples each. Tissue plications with 8, 3, and 4 evenly arrayed staples are shown at 48, 50, and 52 in FIGS. 3A-3C, respectively. Each plication also includes a reinforcing ring 54, 56, 58, respectively, pressed against the side of the plication originally in contact with the staple cartridge. The rings have eyelets for receiving the free ends of all the staples in a group of staples, and form part of the cartridge assembly in the device, one ring per each staple group, where the rings are stacked one against the other, with offset eyelets, on the outer surface of the cartridge, as will be detailed below with reference to FIGS. 11A, 11B, and 14.

The operation of the device as just described is under the control of a piston assembly that will be described further below with respect to FIGS. 5A and 5B. Briefly, a piston assembly in the staple housing has a first hydraulically controlled piston that is movable between retracted and extended positions to (i) move the cartridge support in the staple housing in a distal direction toward the anvil, and at the same time (ii) move the arm assemblies outwardly to draw the anvil housing toward the staple housing. A guide slot in the staple housing limits outward extension of the arm assemblies, establishing a preset spacing between the cartridge and anvil at the tissue-capture position. The staple driver is carried on a second hydraulically controlled piston which is operable to move the staple driver between a retracted position and an extended, staple-ejecting position once a tissue fold has been captured in the device.

Completing the description of what is shown in FIG. 1, device 20 includes an elongate flexible shaft 60 extending between a distal end that is operatively connected to staple housing 22, as shown, and a proximal end (not shown) connected to user controls and by which an operator can control movement of the device in the stomach, and initiate tissue-capture and stapling operations from a position outside the patient's mouth. The shaft contains the various hydraulic-fluid conduits and wire cables, including a vacuum conduit, optionally pairs of compressed-fluid conduits, and force-transmitting cables for positioning the device, as described, for example, in co-owned U.S. Pat. Nos. 8,020,741, 7,922,062, 7,913,892, 7,909,223, 7,909,222, 7,909,219, and 7,708,821, all of which are incorporated by reference herein.

In the description of the embodiments given below, the devices are described as being staplers, and exemplary methods are given with respect to the formation of stapled plications in stomach tissue. It should be understood, however, that the embodiments described herein include features that are easily adapted for applying other types of fasteners, and for applying staples or other fasteners for purposes other than formation of plications. More specifically, the term "staple" is used herein to designate any type of fastener that (i) can be pushed through tissue, and (ii) has one or more leg members that when forced against an anvil are crimped to secure the fastener to the tissue and hold tissue fastened tissue fold together. The disclosed embodiments and methods will also find use in parts of the body where it is useful to make multiple tissue-fold plications.

II. Stapler Construction

FIGS. 4A and 4B are perspective views of head 21 in device 20, with the piston subassembly in the staple housing hidden (4A) and shown (4B). The stapler head is designed to have a minimum profile during insertion to the plication site, and to then transform into a much larger profile device having a large internal volume. For example, in one embodiment the vacuum chamber might have an initial internal volume of 0.2 cubic inches, and an expanded volume of 0.6 cubic inches (i.e. the internal chamber volume after subtracting the volume occupied by the stapler head components positioned within the vacuum chamber). This large internal volume allows a large volume of tissue to be drawn into the vacuum chamber and stapled. In this way, the stapler head creates a relatively large plication without requiring invasive techniques for insertion. In particular, the plication can be sized such that the staples applied to the tissue are well spaced from the edges of the stapled tissue, minimizing the risk of tissue tearing around the staples.

As described above, stapler head 21 generally includes a proximal staple housing 22, a distal anvil housing member 24 and a pair of hinged arm assemblies 26 that operatively connect the two housing for movement toward and away from one another. An expansion bar 32 functions as a membrane raiser and also extends between the staple housing 22 and the anvil housing 24. Although the membrane covering the staple head is not shown, it should be understood that the membrane includes an opening opposite the expansion bar through which tissue is drawn into the tissue chamber, when a vacuum is applied to the chamber.

The staple housing 22 has a base 62 that supports a pair of plates 64 on opposite upper sides of the housing, each plate having a pair of slots, such as slot 66, paralleling the axis of travel of the two housings. A pair of spreader arms 68 is operatively connected to a first driver piston (described below with reference to FIGS. 5A and 5B) through pins 90 that ride in slots 66. The spreader arms are pivotally connected at their opposite ends to arms 28 in the arm assembly, so that movement of the driver piston from a retracted to an extended position within the staple housing moves the inner ends of the spreader arms upwardly in the figure, moving arms assemblies 26 outwardly, and thereby drawing the staple and anvil housing toward one another. This movement is arrested when pins 90 reach the upper ends of slots 66, defining a preselected spacing between the two housings at the capture position of the device.

Figure 5A:
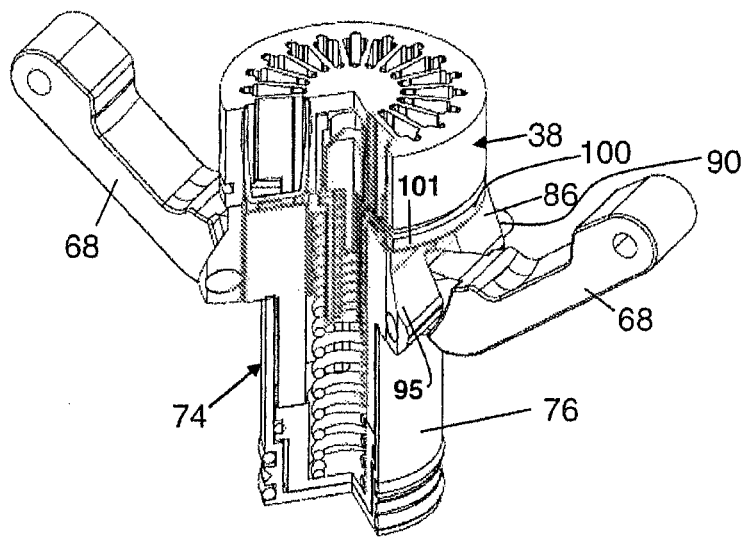
FIG. 5A is a cutaway perspective view of the piston subassembly in the device.
Figure 5B:
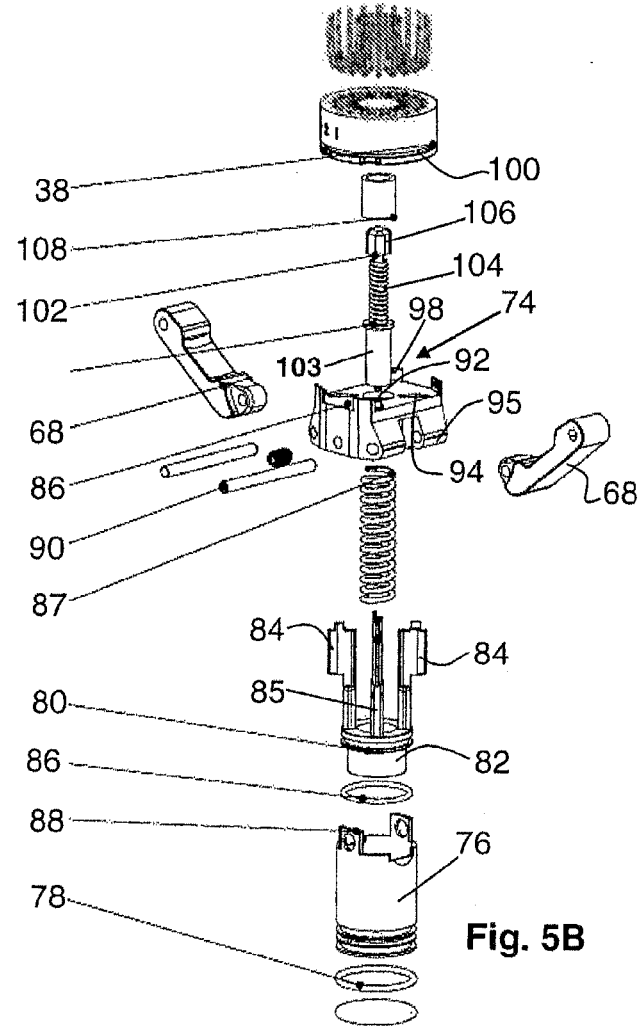
FIG. 5B is an exploded view of the piston subassembly and associated components.

The piston assembly shown in FIG. 4B is illustrated in assembled and exploded views at 74 in FIGS. 5A and 5B. As seen there, the subassembly includes a first hydraulically controlled driver piston 76 that rides within a piston cylinder (not shown) formed in the base of the staple housing. The piston is sealed within the cylinder by an O-ring 78. A staple driver 80 in the subassembly includes a second hydraulically controlled driver piston 82 that rides within a cylindrical cavity formed by piston 76, and a plurality of pusher arms—in this embodiment, four pusher arms 84—carried on the piston that function to eject staples from the cartridge when the second piston is moved from its retracted to expanded position as will be described. A central post 85 mounted on the piston receives a compression spring 87 which biases the staple driver toward its retracted position, as will be seen below, to return the piston to its retracted position after a stapling operation. Piston 82 is sealed within the cylindrical cavity of piston 76 by an O-ring 86 in FIG. 5B.

Carried on first piston 76, for movement therewith between retracted and extended positions, is a cartridge support 86 that serves to releasably support a staple cartridge 38 in housing 22. With reference to FIG. 5B, support 86 is attached to the first piston by fasteners (not shown) that engage eyelets 88 formed at the top of the piston in the figure. With continued reference to this figure, the support provides brackets 95 on opposite sides for pivot attachment of spreader arms 68 to opposite sides of the support, by means of pins 70 extending through holes in the brackets and spreader arms, as seen in FIG. 5B. As noted above, the upward travel of the first piston in the figures is arrested when pins 90 reach the upper ends of slots 66, placing the cartridge and anvil see in FIG. 4b at their tissue-capture position.

With continued reference to FIG. 5B, support 86 has a central opening 92 for receiving post 85 and four peripheral blade-shaped openings 94 for receiving pusher blades 96 carried at the ends of the pusher arms. The construction of the pusher arms in the subassembly are detailed below with reference to FIGS. 6A and 6B. When the second piston is in its fully retracted position, only the upper ends of the blades project through these support openings, and are positioned with respect to the staple cartridge carried on the support such that upper blade ends engage or nearly engage the bottoms (bases) of a group of the staples in the cartridge. When the second piston is activated, and begins moving toward its extended position, the blades eject the staples in a group of staples from the cartridge, through a tissue fold captured in the device, and against anvil 46. At the fully extended position of the piston, the staples have been crimped against the tissue, completing the operation for forming a plication. During the stapling operation, spring 87 becomes compressed between piston 82 and the lower surface of support 86, and serves to bias the second piston to its retracted position once the piston is released, e.g., by release of hydraulic fluid pressure to the piston.

Although the staple driver and cartridge support described above are designed for delivering groups of four staples in a tissue plication, it will be appreciated that different numbers of staples in a group, e.g., 3, 6, or 8, can be accommodated merely by changing the number and positions of the pusher arms on the staple driver, and correspondingly, the number and position of the blade slots in the support.

With continued reference to FIGS. 5A and 5B, the upper surface of support 86 has four snap-in tabs, such as tab 98 (see also FIG. 8A) which engage a lower annular ridge 100 formed on the lower side of cartridge, to secure the cartridge releasably to the support, while still allowing the cartridge to rotate with respect to the support. Also shown in the figure is an indexing spring assembly 102 composed of a sleeve 103, a torsion spring 104 carried in the sleeve, a twist pin 106, and a cartridge insert 108. When a cartridge is placed on the support, insert 108 engages a center core of the cartridge, locking the cartridge to the spring assembly. Before being snapped onto the support, the cartridge is rotated manually, to tension spring 104 so that it urges the cartridge in the direction of spring force. The indexing mechanism by which the cartridge is rotated slightly, after each stapling operation, to advance the cartridge to the next-up group of staples will be detailed below with respect to FIGS. 8A and 8B. The cartridge assembly, including cartridge 38, staples held in the cartridge, and reinforcing rings used to strengthen the stapled tissue plications, will be described in the section below with respect to FIGS. 11-15.

Figures 6A, 6B:
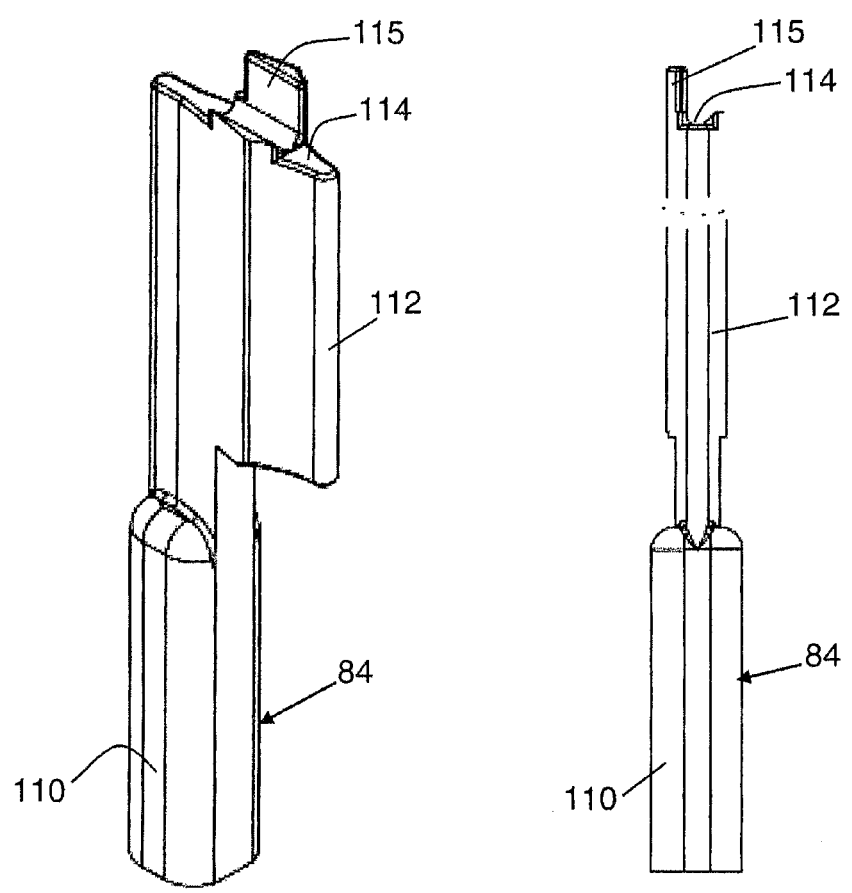
FIGS. 6A and 6B are side (6A) and perspective (6B) views of stapler pushers in the device.

FIGS. 6A and 6B illustrate a representative pusher arm 84 in staple driver 80. The flag-shaped arm includes a lower post 110 and an upper blade 112 which is widened in its middle section for strength. The blade is dimensioned in length to support substantially the entire base portion of a staple within an elongate trough 114 formed at the upper end of the blade. As seen in FIG. 6B, the trough is tapered on its sides to assist in guiding the base of a staple into a fully centered position on the blade. A tab 115 projecting upwardly from the edge of the blade serves as a stop in the indexing mechanism in the device, as will be described below with reference to FIGS. 8A and 8B.

Figure 7A:
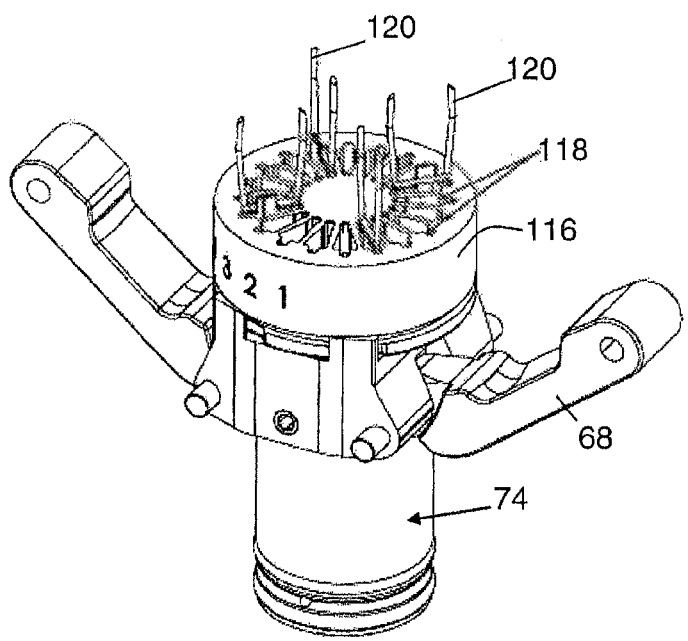
FIGS. 7A and 7B are perspective views of the piston subassembly in the device showing the stapler firing a first set (7A) and a fourth set (7B) of four staples.
Figure 7B:
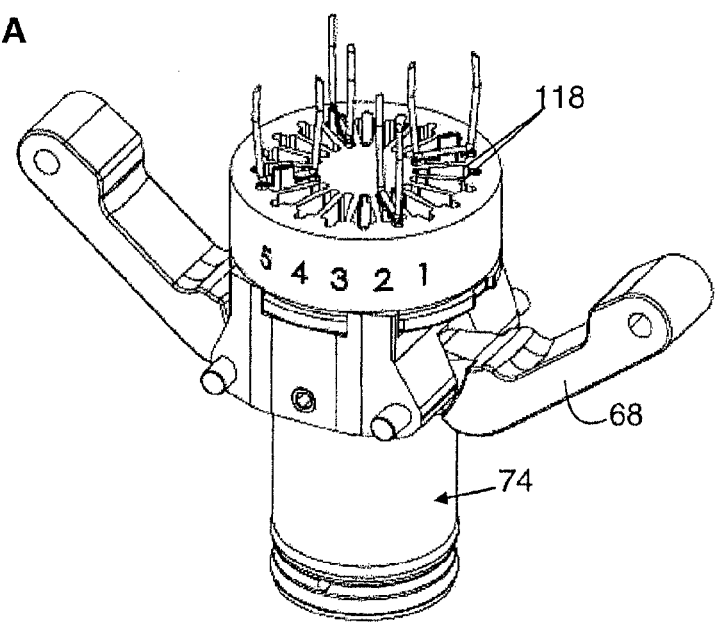

FIGS. 7A and 7B illustrate the operation of the piston subassembly with successive stapling operations. The cartridge in this particular embodiment, indicated at 116, has 20 slots, such as slots 118, divided into 5 groups, each having 4 staples. In FIG. 7A, the cartridge is positioned so that the staples in a first group in the cartridge, such as staples 120, are aligned with the four blades in a staple driver having a rotationally fixed position. The figure shows the staples being ejected from the first-group slots by activation of the staple driver to its extended stapling position. After the staples are ejected from the cartridge, an indexing mechanism in the piston subassembly advances the cartridge to the second-group position, where the pusher arm blades are aligned with staples in the second-group slots in the cartridge. FIG. 7B illustrates the condition of the subassembly after three such stapling operations, where the staple driver is now positioned so that staples in the fourth group in the cartridge, such as staples 122, are ejected from the cartridge when the staple driver is activated.

As just illustrated, the indexing mechanism in the device functions, after each stapling cycle, to advance the staple cartridge relative to the staple pusher, to position a next-up group of staples in the cartridge for engagement with associated arms in the staple driver. The indexing mechanism may function to advance the cartridge incrementally, with the staple driver held in a fixed angular position, or to advance the staple driver incrementally, with the cartridge held in a stationary position. The first approach is the one adopted in the presently described embodiment, and an exemplary implementation is described below with reference to FIGS. 8A and 8B. The second approach is illustrated in FIG. 9.

FIG. 8A shows the piston subassembly described above with reference to FIGS. 5A and 5B, but shown here with the cartridge assembly removed, and represented only by two groups of staples, 124, 126 in the assembly. In the figure, staples 124 in a first group of staples are biased by torsion spring 104 against pusher arm tabs 115 projecting through associated blade openings in support 72, preventing the cartridge from rotating further in a counterclockwise direction, i.e., in the direction urged by spring 104. When this first group of staples is ejected from the cartridge, and when the staples are fully ejected from their slots in the cartridge, the cartridge is now urged by spring 104 in a counterclockwise direction until a next group of staples 126 makes contact with the pusher arms. As can be appreciated in FIG. 8B, when the pusher arms are fully retracted, the base portions of the staples are in contact only with the pusher arm tabs. Then, as the pusher arms are moved upwardly in the figures with the next stapling operation, the bases of the tab-engaged staples seat themselves in the pusher arm troughs 114, and this next-up group of staples is ejected from the cartridge, freeing the cartridge to advance to the third group of staples.

Several other indexing mechanisms for advancing the cartridge incrementally during operation are contemplated. In one embodiment, spring 104 is replaced a hydraulic or magnetic or electromagnetic element effective, when activated to apply a constant biasing force to the cartridge, to bias it in the direction of incremental rotation, or to apply a short-duration force effective to advance the cartridge by one staple group. In another general embodiment, the staple cartridge has multiple side projections dimensioned to engage a stop member in the staple housing only as long as a staple is present in the associated slot. Then, as a staple in each successive slot is ejected, and the associated projection is neutralized, e.g., broken or allowed to retreat into the staple slot, the cartridge advances to the next projection at the next-up group of staples.

Figure 9:
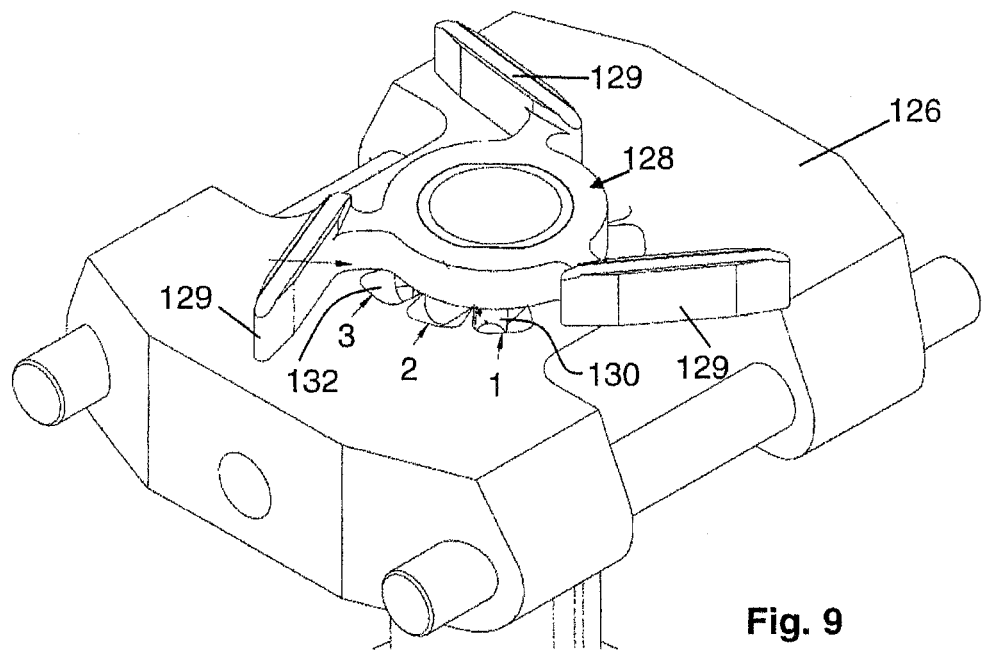
FIG. 9 shows portions of an alternative pusher assembly in a stapling device of the invention, with a three-arm pusher and an indexing mechanism for aligning a rotated pusher with slots in a stationary staple cartridge.

FIG. 9 illustrates an indexing mechanism in which the cartridge in the device is held at a fixed position and the staple driver is moved incrementally. The figure shows the upper surface of a cartridge support 126 and a pusher arm assembly 128 carried at the distal end of a staple driver, and having three pusher arms 129. The arm assembly is biased to rotate in a clockwise direction in the figure by a torsion spring (not shown) interposed between the staple driver and cartridge support. The cartridge is open in its lower region to accommodate the driver pusher arms, and is releasably mounted on the support by snap-in tabs tables (not shown). Projecting outwardly from the arm assembly shaft, immediately below the arm assembly, is a pin 130 fashioned to reside in one of multiple asymmetric slots 132 in the upper surface of the support 126. In the stapler configuration shown in the figure, pin 130 resides in a first slot 132 that aligns pusher arms 129 with the three slots representing the first group of staples in the cartridge. When the staple driver is activated for stapling, the three pusher arms engage the slots in the first-group before pin just before pin 130 is lifted out of slot 132, preserving the alignment between the pusher assembly and first-group slots. After the staples are ejected and the staple driver is returning to its retracted position, the asymmetry of the slots 132 will allow the staple driver to rotate incrementally at the moment pusher arms 129 disengage from the cartridge slots, placing pin 130 in the second slot 132, and aligning the pusher arms with the next group of staples in the cartridge.

Other index mechanisms for incrementally rotating the staple driver with respect to a stationary cartridge are contemplated. For example, the staple driver shaft rotational position could be controlled by a hydraulic or electronic pulse, or by replacing the torsion spring with a magnetic or electromagnetic biasing force. Alternatively, the staple driver shaft could have a cammed element that interacts with a stationary element in the staple housing to rotate the staple driver incrementally as it returns to its fully retracted position after each stapling operation.

Figure 10:
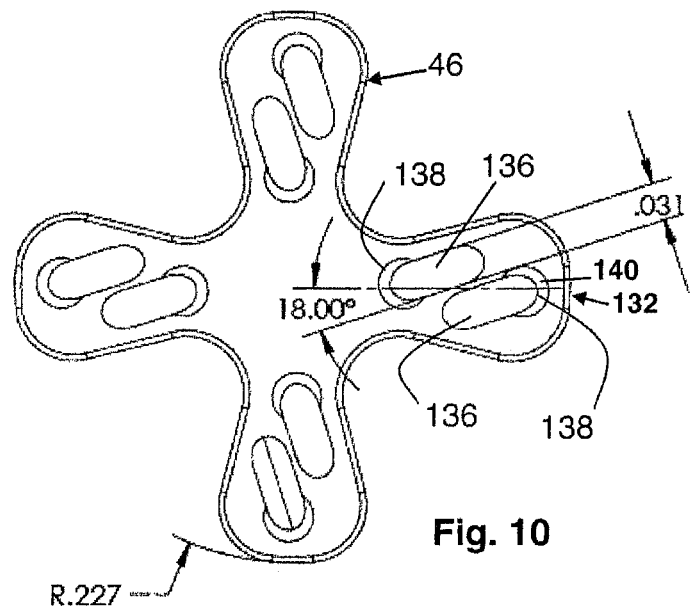
FIG. 10 is a planar view of an anvil in the stapling device of the invention.

FIG. 10 is a planar view of an anvil 46 designed for use in a device that ejects four staples at each stapling cycle, showing the anvil surface contacted by the staples. The anvil has four arms 134, each providing a pair of capsule-shaped, recessed areas 136. The areas are arranged on each arm surface such that a line 140 extending along the middle of the arm intersects opposite ends 138 of the two areas, and forms an angle of about 18° with the long axis of each recessed area, as seen. Since each recessed area guides the direction of bending of the staple legs, as they are forced against the anvil, the two staple legs will assume the side-by-side configuration of the recessed areas themselves, thus preventing the staple legs of a staple from colliding and interfering with one another during stapling.

III. Cartridge Assembly

FIGS. 11-15 show details of the cartridge assembly 36 in the staple device. As seen in FIGS. 11A and 11B, the assembly includes cartridge 38 providing a plurality of staple slots 40, staples 42 received in the slots, and a plurality of reinforcement rings, such as rings 136, 138, 140 that are stacked on the upper surface of the cartridge as will be discussed below with reference to FIG. 14.

Figures 11A, 11B:
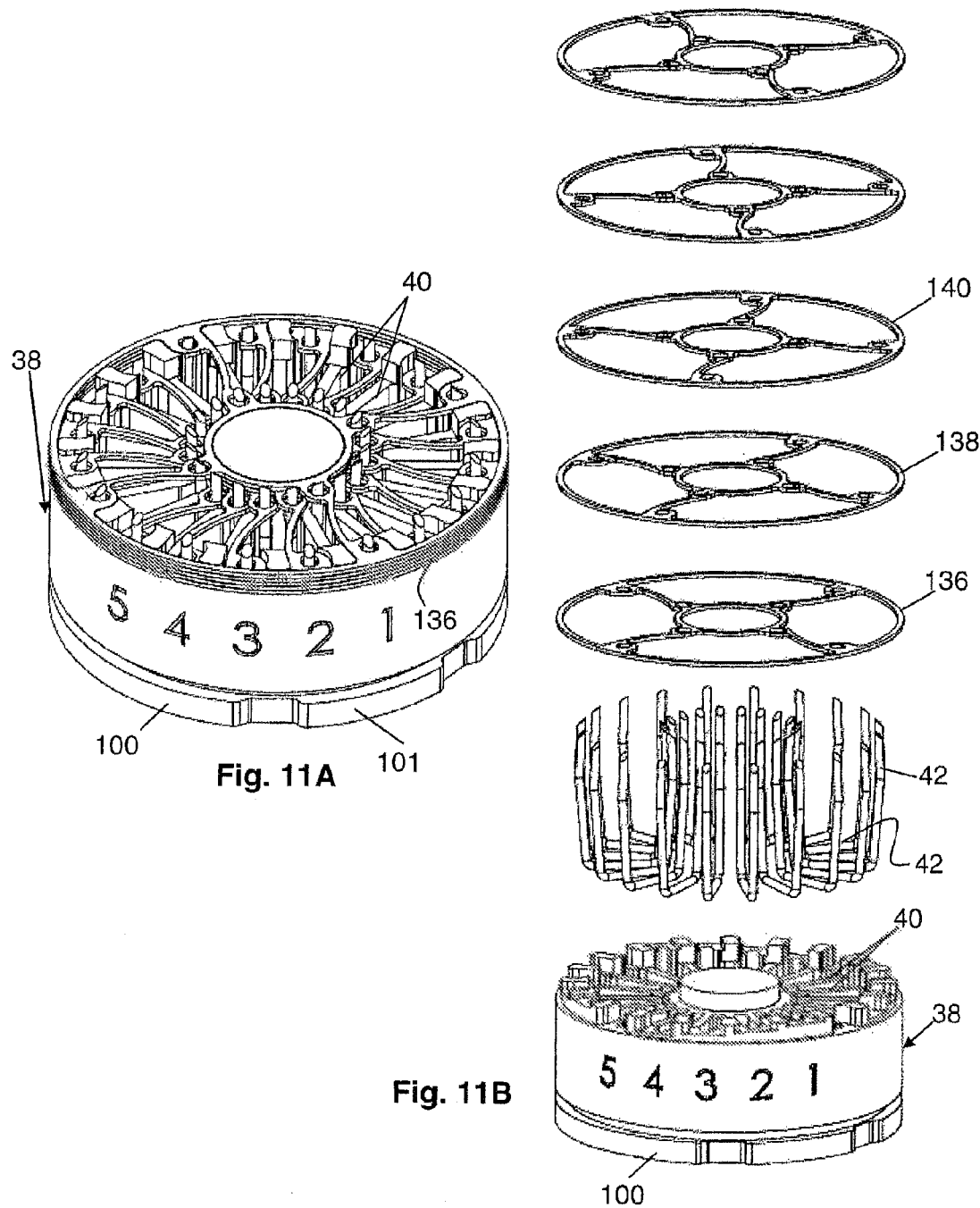
FIG. 11A is a perspective view of a staple cartridge assembly in the device.
FIG. 11B shows the same assembly in exploded view.

The slots in cartridge extend in a generally radial direction within the annular body of the cartridge as seen in the FIG. 11A. As indicated above, the cartridge preferably provides N×M slots circularly arrayed around the cartridge body, where N is the number of groups of slots and M, the number of slots in each group. The cartridge shown has 20 slots which are divided into 5 groups of 4 slots each, as indicated, although the same cartridge would be suitable for a stapler designed to eject any N×M combination 20 staples, e.g., 4 groups of 5 staples each. The opposite sides of the slots have a slight inward taper in cross-section, for a purpose to be described, and are dimensioned to hold the staples snugly but not tightly, so that the staples can be readily ejected from their slots. An annular ridge 100 formed on the lower end of the cartridge is used for mounting the cartridge rotatably on cartridge support 72, as described above. The cartridge is typically formed as a single-piece molded plastic article, and has a typical diameter between 1 and 1.5 cm and height dimension between 0.3 and 1 cm.

Figure 12A:
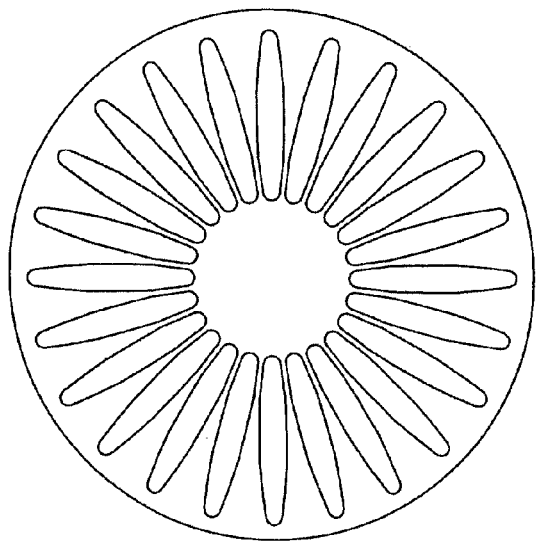
FIGS. 12A-12D are plan views showing various slot configurations in a staple cartridge of the invention with radial alignment for 24 (12A) and 16 (12B) staples and 45° offset for 24 (12C) and 16 staples (12D)
Figure 12B:
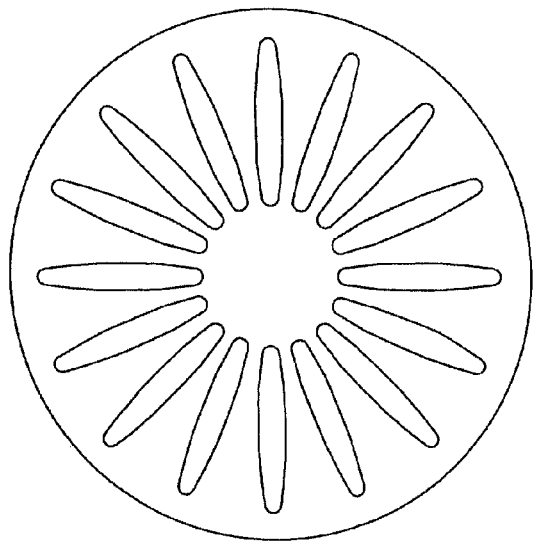
Figure 12C:
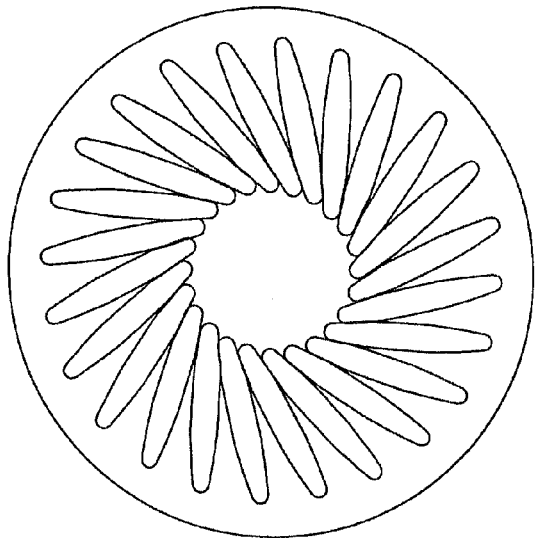
Figure 12D:
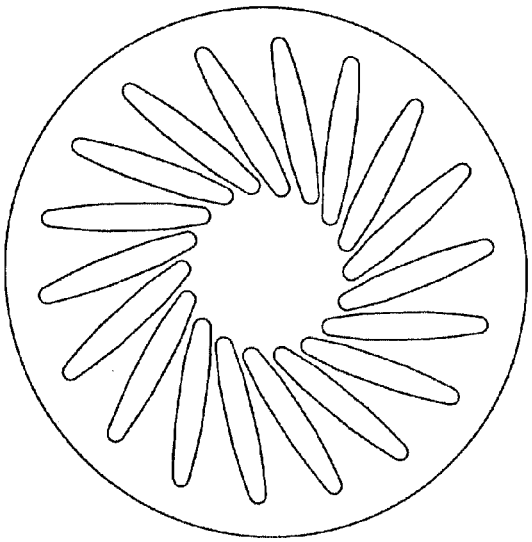

FIGS. 12A-12D are plan views showing different numbers and arrangement of slots in a cartridge of the invention. FIGS. 12A and 12B shows arrangements of 24 and 16 slots, respectively, oriented in strictly radial directions. FIGS. 12C and 12D shows arrangements of 24 and 16, slots, respectively, oriented in radially offset directions. The latter configuration shortens the radial extent of the slots, allowing for wider staples if needed.

Figure 13:
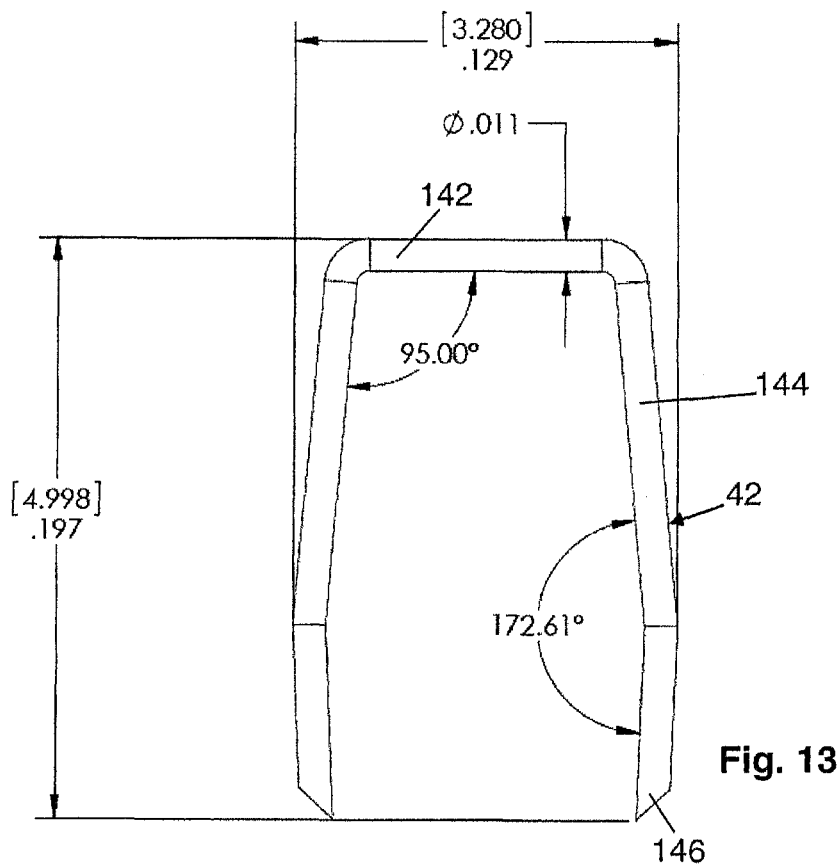
FIG. 13 is an enlarged side view of a staple for use in the stapler.

An exemplary staple 42 for use in the cartridge is shown in FIG. 13, and includes a base 142 and a pair of bowed staple legs 144 terminating at beveled staple ends or tips 146. The bow in the staple legs is a slight taper on progressing from a point 148 along the legs toward the staple base, matching the slight taper in the cartridge slots in cross section, to support the staples in the slots at a desired vertical position that disposes the staples' bases in the cartridge for the desired interactions with the staple pusher, as described above with reference to FIGS. 8A and 8B. The staple ends are beveled in an inner-to-outer direction in the FIG. 13, to urge the ends of the staple legs toward one another when the staple is ejected against the anvil, as well as provide sharpened tips.

Figure 14A:
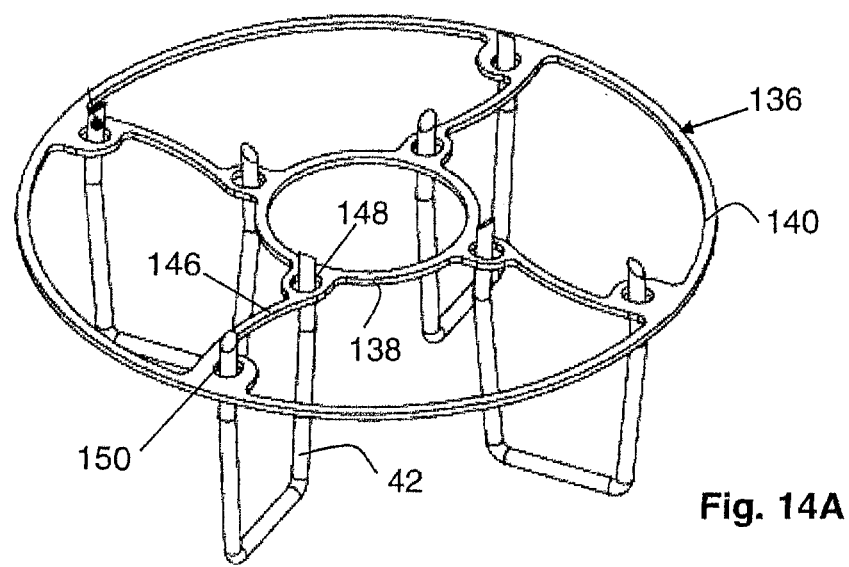
FIGS. 14A and 14B are perspective views of a reinforcing ring shown with a corresponding group of staples in an assembled (14A) and partially stapled condition.
Figure 14B:
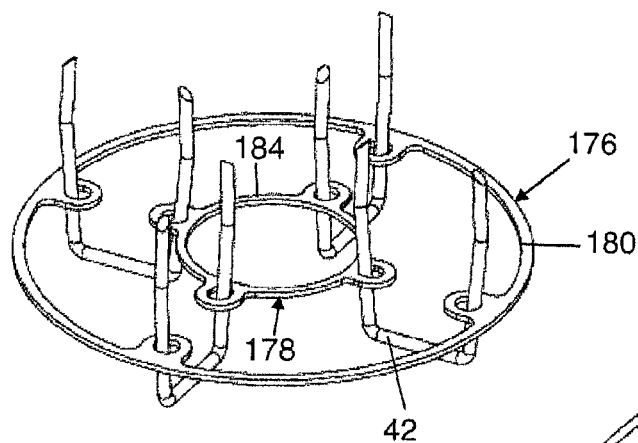
Figure 15A:
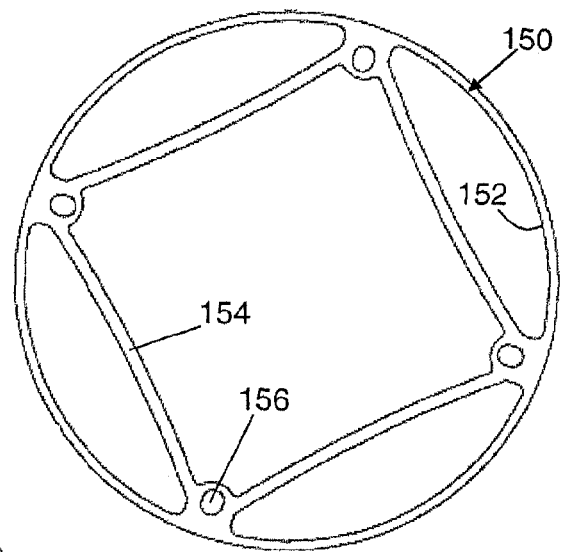
FIGS. 15A-15D shows alternative configurations of a reinforcing ring suitable for use in the invention.
Figure 15B:
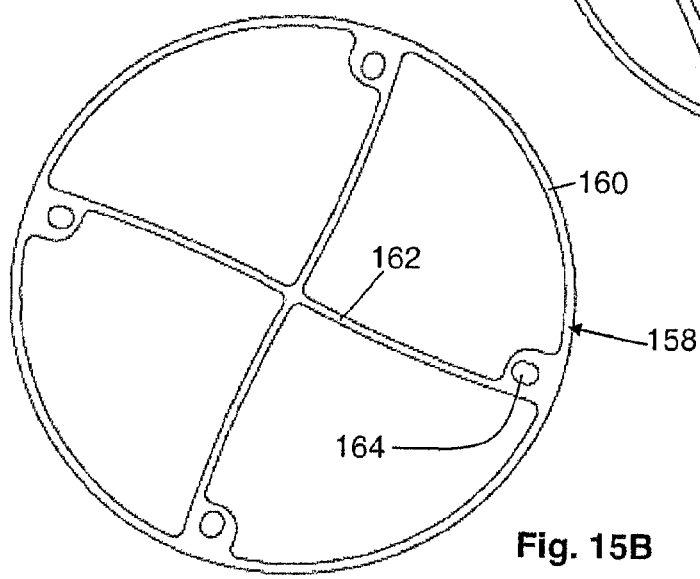
Figure 15C:
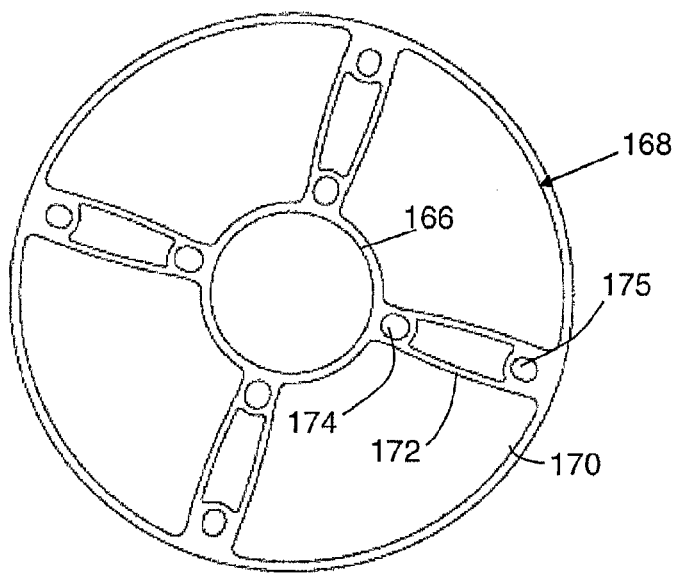
Figure 15D:
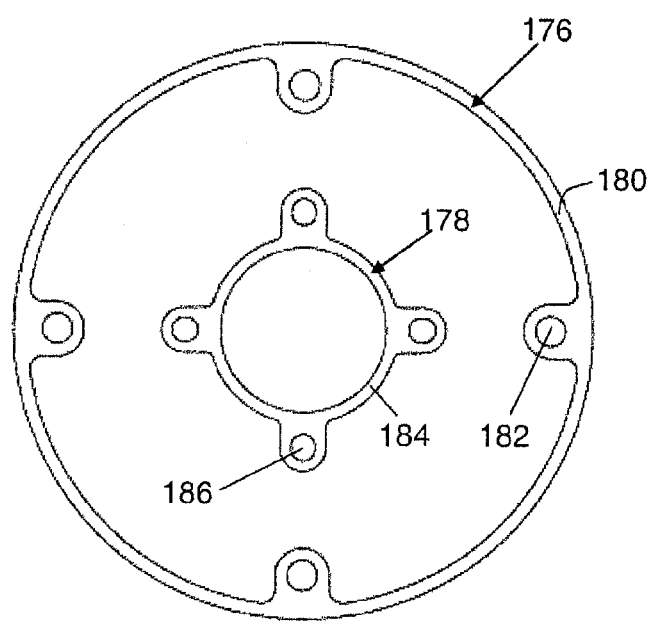

An exemplary reinforcing ring in the cartridge assembly is shown at 136 in FIG. 14. The ring includes inner and outer ring members 138, 140 respectively, connected by spokes 142 and inner and outer eyelets 144, 146, respectively, that receive the ends of associated staples 42 in the fully assembled condition. As seen in FIG. 11B, after staples 42 are loaded into their respective slots, the reinforcing rings are stacked on the assembly, with the eyelets in each successive ring, in a top-to-bottom direction, receiving the staple ends in the staples in each successive group, starting with the first group (top ring), then the second ring (second ring from the top) and so on. Thus as each group of so staples is ejected, it carries the top-most ring against the tissue-fold being stapled. The relative positions of a staple and ring during stapling are shown in FIG. 14B, just before the base of the staple engages the ring and presses it against the tissue fold being stapled. The ring shown here is the two-section ring described below with reference to FIG. 15D.

Various alternative configurations in a reinforcing ring in the cartridge assembly are shown in FIG. 15A-15D. The ring shown at 150 in FIG. 15A includes an outer ring member 152 having four cross-members 154 that join the outer ring at eyelets 156 that in turn receive only the outer leg of a staple. Ring 158 shown in FIG. 15B has a similar construction, with an outer ring member 160 and four radial legs 162 joined to the outer ring member at eyelets 164 that in turn receive the outer leg of a staple only. Ring 166 in FIG. 15C has inner and outer ring members 166, 168, respectively, joined by cross bars 172, with inner and outer eyelets 174, 175 receiving the opposite ends of the staples. The ring 176 shown in FIG. 15D has two separate ring members 178, 180, each with separate eyelets 182, 184 for receiving outer and inner ends of the staples. The two ring members require separate assembly on the cartridge once the staples are in place.

Although not shown here, the cartridge assembly may have a simplified construction in which a circular array of staples is held in place by a frangible polymer webbing or film to which the staples are attached. In this embodiment, the webbing or film serves as the cartridge, and ejection of a group of staples from the cartridge serves to separate those staples from the structure.

It can be appreciated from the above how various objects and features of the invention are met. The stapling device, once loaded with a fresh cartridge assembly, can be inserted into a patient's stomach, and multiple tissue plications formed with anywhere from 2 to 8 staples, and optionally, each strengthened by a reinforcing ring. If more than a given number of plications are required, e.g., more than 8 plications, the device can be removed and quickly reloaded with a fresh cartridge assembly, but in any case, a single cartridge reload during an operation should be sufficient to accomplish almost any stomach reduction or repair operation.

Any and all patents, patent applications and printed publications referred to above, including those relied upon for purposes of priority, are incorporated herein by reference.

It is claimed:

1. A stapling device for use in producing multiple stapled tissue plications without needing to reload the device between successive plications comprising, in operative condition
    (a) a staple housing having a cartridge assembly support mounted therein,
    (b) a cartridge assembly held on said support and comprising a cartridge having multiple groups of offset staple slots, where the slots in each group are circularly arrayed about a cartridge assembly center axis and are oriented outwardly with respect to said axis, and staples held in the slots,
    (c) a staple driver mounted in said housing for movement between retracted and extended positions, said driver including a pusher having a plurality of arms for engaging the staples in a first group of staples in said cartridge, and ejecting such staples from the cartridge, when the staple driver is moved from a retracted toward an extended position,
    (d) an indexing mechanism in said staple housing for advancing the staple cartridge relative to the staple pusher, to position a next-up group of staples in the cartridge for engagement with associated arms in the pusher, after the staples in the previous group have been ejected from the cartridge, and
    (e) an anvil housing having an anvil, said staple housing and anvil housings being mounted for relative movement with respect to each other, under the control of a housing driver in one in one of said housings, toward and away from a stapling position at which a tissue fold disposed between the two housings is captured for stapling between the cartridge assembly and anvil,
    wherein successive stapled tissue folds can be formed without reloading the device by successively stapling tissue folds captured between the cartridge assembly and anvil with staples from successive offset groups of staples in the cartridge assembly.

2. The device of claim 1, wherein the cartridge includes an outer surface, the staples in the cartridge each have a pair of free ends projecting from the cartridge's outer side, and the cartridge assembly further includes multiple reinforcing rings stacked against the cartridge's outer side, where each ring has a plurality of circularly arrayed eyelets for receiving therein, one or both of the free ends of the staples in a given staple group, such that one ring is stacked against the cartridge assembly for each group of staples, and the groups of staples are ejected in the order of the stacked rings, in an outer to inner direction.

3. The device of claim 1, wherein the cartridge includes N groups of M slots each, where N and M are each at least 3, and N×M is at least twelve.

4. The device of claim 1, wherein the pusher arms provide troughs into which the staples are received during a staple ejection operation, and the troughs have rounded sides for guiding the staples into the centers of the troughs.

5. The device of claim 1, wherein the cartridge is mounted on the cartridge assembly support for angular movement with respect to the holder, and the indexing mechanism includes a torsion spring operatively interposed between the cartridge and the cartridge support, for advancing the cartridge to a next-up indexing position when the staples in a previous group of staples have been ejected and as the pusher is moved toward its retracted position.

6. The device of claim 5, wherein the indexing mechanism further includes a tab on at least the pusher that engages at least one of the staples the in next-up group of staples in the cartridge as the pusher is moved toward its retracted position.

7. The device of claim 1, wherein the cartridge assembly is mounted on the cartridge holder at a fixed position, and the indexing mechanism includes a torsion spring operatively interposed between the cartridge support and the cartridge, for advancing the pusher arms to a next-up indexing position in the cartridge when the staples in a previous group of staples have been ejected and as the pusher is moved toward its retracted position.

8. The device of claim 7, wherein indexing mechanism further includes a tab on at least one of the pusher arms that engages the next-up slot on the cartridge assembly as the pusher is moved toward its retracted position.

9. The device of claim 1, wherein the staple cartridge is releasably support on the cartridge support.

10. The device of claim 1, wherein the staple cartridge is a cylindrical magazine whose multiple groups of offset staple slots extend through the cartridge assembly and are tapered at the bottom of the slots to retain the staples therein.

11. The device of claim 10, wherein the slots formed in the cartridge extend along radii projecting from the central axis of the cartridge.

12. The device of claim 10, wherein the slots formed in the cartridge are radially offset from one another, such that a radial line that intersects the inner end of a slot intersects a second slot between its inner and outer ends.

13. The device of claim 1, wherein the staples are U-shaped, and the staple legs are bowed outwardly, such that the legs taper inwardly on progressing toward the base of the staple, and taper inwardly on progressing toward the free ends of the staples.

14. The device of claim 1, wherein the anvil includes a plurality of anvil surfaces, one for each staple in a group, and each surface includes a pair of side-by-side grooves for staple bending a staple being ejected against the anvil so that the ends of the staples are bent into a side-by-side overlapping configuration.

15. The device of claim 1, wherein said staple and anvil housings are mounted by an arm assembly in the device, for movement toward and away from one another, and said housing driver operatively couples the staple housing to the arm assembly, such that movement of the housing drive from a retracted toward an extended position causes the arm assembly to spread outwardly and move the anvil housing relatively toward the staple housing.

16. The device of claim 15, wherein the arm assembly includes at least a pair of arms, each of which pivots outwardly as the anvil housing is drawn relatively toward the staple housing, said arms forming, along with confronting surfaces of the staple cartridge assembly and anvil, a tissue chamber that expands outwardly as the two housing are drawn toward one another.

17. A staple cartridge assembly for use with a stapling device for producing multiple stapled tissue plications without needing to reload the device between successive plications comprising,
(a) a staple cartridge having multiple groups of offset staple slots, where the slots in each group are circularly arrayed about a cartridge center axis and are oriented outwardly with respect to said axis,
(b) staples held in the slots, and having a pair of free ends that extend from an outer surface of the cartridge, and
(c) multiple tissue-fastening rings stacked against the cartridge's outer surface, each ring having a plurality of circularly arrayed eyelets for receiving therein, the free ends of the staples in a given staple group, such that one ring is stacked against the cartridge assembly for each group of staples, and the groups of staples are ejected in the order of the stacked rings, in an outer to inner direction.

18. The cartridge assembly of claim 17, wherein the staple cartridge is a cylindrical magazine whose multiple groups of offset staple slots extend through the cartridge assembly and are tapered at the bottom of the slots to retain the staples therein.

19. The device of claim 18, wherein the slots formed in the cartridge extend along radii projecting from the central axis of the cartridge.

20. The device of claim 19, wherein the slots formed in the cartridge are radially offset from one another, such that a radial line that intersects the inner end of a slot intersects a second slot between its inner and outer ends.

* * * * *